United States Patent [19]

Robb

[11] Patent Number: 5,215,533

[45] Date of Patent: Jun. 1, 1993

[54] SAFETY SYRINGE INCORPORATING VACUUM RETRACTION OF THE NEEDLE

[75] Inventor: Darryl G. Robb, Gympie, Australia

[73] Assignee: Robb Pascal Patent Pty. Ltd., Alderley, Australia

[21] Appl. No.: 720,499

[22] PCT Filed: Sep. 17, 1990

[86] PCT No.: PCT/AU90/00426

§ 371 Date: Jul. 18, 1991

§ 102(e) Date: Jul. 18, 1991

[87] PCT Pub. No.: WO91/04065

PCT Pub. Date: Apr. 4, 1991

[30] Foreign Application Priority Data

Sep. 18, 1989 [AU] Australia .................. PJ6435

[51] Int. Cl.⁵ ........................................ A61M 5/32
[52] U.S. Cl. ................................ 604/195; 604/110;
604/198; 604/222
[58] Field of Search ............... 604/110, 140, 143, 146,
604/187, 195, 208–211, 218, 222, 240, 225, 192,
198

[56] References Cited

U.S. PATENT DOCUMENTS

| | | |
|---|---|---|
| 3,669,111 | 6/1972 | Duboer . |
| 4,246,898 | 1/1981 | Travalent et al. . |
| 4,766,908 | 8/1988 | Clement . |
| 4,772,265 | 9/1988 | Walter . |
| 4,826,484 | 5/1989 | Haber et al. .................. 604/195 |
| 4,828,548 | 5/1989 | Walter ........................... 604/143 |
| 4,838,869 | 6/1989 | Allard ............................ 604/195 |
| 4,874,382 | 10/1989 | Lindemann ................... 604/195 |
| 4,955,869 | 9/1990 | Bin ................................ 604/110 |
| 4,955,870 | 9/1990 | Ridderheim et al. .......... 604/195 |
| 5,019,044 | 5/1991 | Tsao ............................. 604/195 |

FOREIGN PATENT DOCUMENTS

| | | |
|---|---|---|
| 0593226 | 2/1960 | Canada .......................... 604/195 |
| 0326983 | 8/1989 | European Pat. Off. . |
| 8904681 | 6/1989 | PCT Int'l Appl. ............. 604/110 |
| 874876 | 8/1961 | United Kingdom . |
| 9012612 | 11/1990 | World Int. Prop. O. ....... 604/110 |

Primary Examiner—John D. Yasko
Assistant Examiner—Ronald Stright, Jr.
Attorney, Agent, or Firm—Jacobson, Price, Holman & Stern

[57] ABSTRACT

A safety syringe for preventing "needle stick" injury and/or reuse of the syringe includes a body (2), a plunger (4) mounted within the body, connection means (24) for connecting the plunger (4) to a needle holder (6) whereby subsequent retraction of the plunger (4) withdraws the needle holder (6) and the needle with a shielded position within the body (2) effected by a vacuum chamber (18) defined between the plunger (4) and the syringe body (2), vacuum being created within the chamber (18) by movement of the plunger (4) during the injection stroke and serving to withdraw the plunger (4), the needle holder (6) and needle after injection pressure is removed. The syringe may be provided with braking means (20) to control the rate of withdrawal of the needle and/or to prevent withdrawal until the injection stroke of the plunger (4) has been completed.

17 Claims, 6 Drawing Sheets

SAFETY SYRINGE INCORPORATING VACUUM RETRACTION OF THE NEEDLE

FIELD OF THE INVENTION

The present invention relates to a syringe, and more particularly to a safety syringe for preventing contamination, fear of contamination and physical injury by "needle stick" by the syringe needle after use and/or for preventing reuse of the syringe.

BACKGROUND OF THE INVENTION

In order to minimize the risk of contamination from a used syringe, it is common practice for used syringes to be deposited into heavy duty plastic bins which cannot be pierced by the needles. The bin and contents are then moved to a disposal facility at which they are incinerated. This means of disposal is of limited effect as it does not eliminate "needle stick" risk between needle use and disposal. Current disposal methods are also relatively expensive.

Numerous attempts have been made to design an acceptable syringe in which, after use, the needle is withdrawn into the body of the syringe and retained there in some manner. These designs are all directed to the same end of covering the needle after use to prevent inadvertent "needle stick" injuries with their attendant risk of cross-infection and to prevent reuse of the syringe. In many of these prior art arrangements the withdrawal of the needle into the body is entirely manual and requires the syringe user to remember to make some deliberate relative movement, normally between the plunger and the body, to effect withdrawal of the needle into the body of the syringe. Proposals have been made, as in Australian Patent Specifications 593,513, 594,634 and 35,676/89, to induce automatic withdrawal of the plunger into the body by the use of a helically coiled spring. This necessitates the use of additional and costly parts in the syringe and complicates its assembly.

In its first aspect the present invention is directed to an alternative arrangement for the automatic withdrawal of a syringe needle into the body of the syringe.

The above Prior art proposals for automatic withdrawal of the plunger have the disadvantage that immediately upon removal of the positive manual pressure holding the plunger in a depressed condition the spring will immediately stop movement of the plunger to its extended condition and simultaneously commence withdrawal of the needle into the body of the syringe. This could cause tissue tear and inadvertent and unwanted suction of blood into the syringe unless the operator consciously keeps the plunger depressed until the syringe is fully withdrawn from the patient's body. In a second aspect the present invention provides braking means to slow at least the initial rate of withdrawal of the needle into the body of the syringe.

BRIEF SUMMARY OF THE INVENTION

According to a first aspect of the present invention there is provided a syringe comprising a body, a plunger mounted within the body, means for connecting the plunger to a needle holder at the end of an injection stroke of the plunger whereby subsequent retraction of the plunger withdraws the needle into a shielded position within the body, and energy storage means energizable by the insertion stroke to cause such withdrawal of the plunger and needle after the injection stroke. The energy storage means comprises a vacuum chamber defined between the plunger and the syringe body, vacuum being created within the chamber by movement of the plunger during the injection stroke, said vacuum serving to withdraw the plunger and needle after injection pressure is removed.

According to a second aspect of the present invention there is provided a syringe comprising a body, a plunger mounted within the body, means for connecting the plunger to a needle holder at the end of an injection stroke of the plunger whereby subsequent retraction of the plunger withdraws the needle into a shielded position within the body, and energy storage means energizable by the insertion stroke to cause such withdrawal of the plunger and needle after the injection stroke, resilient braking means being disposed within the space defined between the body and the plunger, and being disposed on one of them and bearing against the other sufficiently to retard but not stop the withdrawal of the plunger and needle after the injection stroke.

In a preferred embodiment of the second aspect of the invention the resilient braking means is formed integrally with sealing means defining one end of the vacuum chamber of the first aspect of the invention. It is to be understood, however, that the resilient braking means could be applied to a syringe in which the energy storage means is other than a vacuum chamber.

It is preferred that the resilient braking means is moveable longitudinally of that one of the body and the plunger to which it is affixed so as to alter the braking force it applies to the other of those members. This allows the withdrawal of the plunger under the action of the vacuum chamber to be prevented until the completion of injection stroke of the plunger if desired.

In a third aspect the present invention consists in a syringe comprising a body, a plunger mounted within the body, means for connecting the plunger to a needle holder at the end of an injection stroke of the plunger whereby subsequent retraction of the plunger withdraws the needle into a shielded position within the body, stop means attached to the body or to the plunger to prevent depression of the plunger into the body sufficient to connect the plunger to the needle holder in a first stroke of the plunger into the body, engagement means on the other one of the body or the plunger to engage the stop means upon completion of the first stroke of the plunger and to render the stop member inoperative upon a first retraction of the plunger to draw an injectable liquid into the syringe following the first stroke such that the plunger may be connected to the needle holder on completion of the following injection stroke.

BRIEF DESCRIPTION OF THE DRAWINGS

The invention will now be further described with reference to the accompanying drawings wherein;

FIGS 2a-2e are five longitudinal cross-sectional views through a syringe according to another embodiment of the present invention, FIG. 2a showing the syringe in the condition in which it is shipped for use, FIG. 2b showing the syringe in a condition ready to draw up an injectable liquid, FIG. 2c showing the syringe in a condition in which the liquid has been drawn up and the dose of the liquid is about to be selected with an accompanying exclusion of air from the syringe, FIG. 2d shows the syringe in a condition immediately after the injection has been given, and FIG. 2e shows the syringe in a condition after the needle has been automatically withdrawn into the syringe body;

DETAILED DESCRIPTION

Figure 1A:
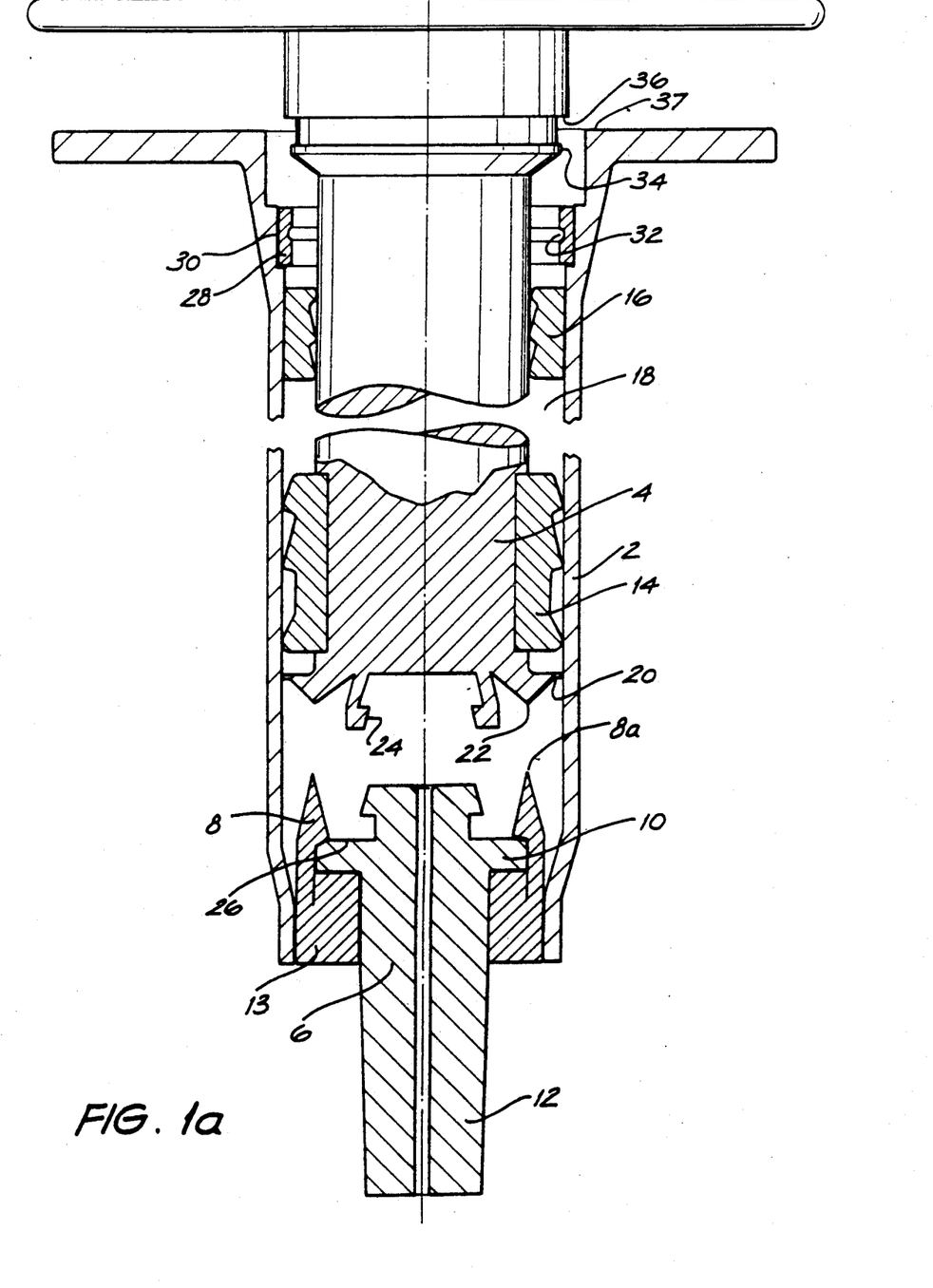
FIG. 1a is a schematic longitudinal cross-section of a syringe in accordance with the preferred embodiment of the invention showing the syringe in a condition prior to use.
Figure 1B:
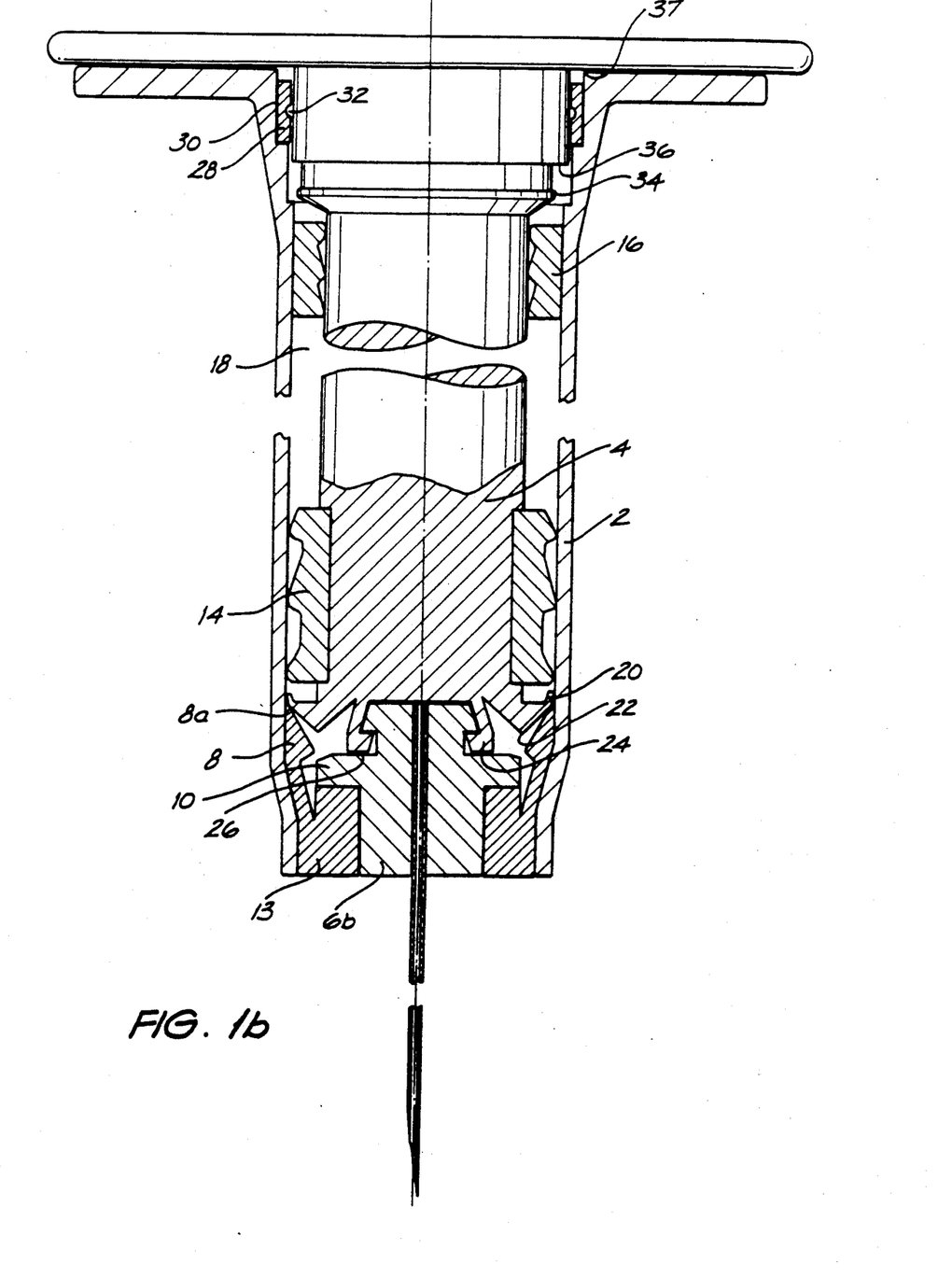
FIG. 1b is a view similar to FIG. 1a showing the syringe in a condition at the end of its injection stroke in engagement with the needle holder for the syringe needle.

The syringe shown in FIGS. 1a and 1b comprises a body 2 and a plunger 4 mounted within the body 2. A needle holder 6 is mounted at the forward or inner end of the body 2 by means of an annular array of releasable locking pawls 8 which normally engage over a shoulder 10 of the holder 6 in order to prevent retraction of the holder 6 into the body 2. A forwardly-projecting part 12 of the needle holder 6 is of conventional form in order to mount a standard needle which is a friction fit on the holder. Alternatively the body 2 can mount a needle with an integral holder 6b as shown in the lower part of FIG. 1b, the holder 6b co-operating with the releasable pawls 8 in the same manner as the holder 6. The pawls 8 extend rearwardly from a sleeve 13 which centers the needle holder in the body 2.

The plunger 4 carries, towards its forward end, an annular travelling seal 14 in sliding contact with the inner surface of the syringe body 2. The seal 14 is intended to form a high quality hermetic seal and is shaped to define a series of axially spaced annular sealing zones against the body 2. A similar high quality annular seal 16 is fixedly mounted on the body 2 towards its rear or outer end. This fixed seal 16 has on its inner surface a series of annular sealing zones which seal against the outer surface of the plunger 4. The space 18 defined between the two seals 14, 16 constitutes a vacuum chamber. Upon actuation of the syringe the movement of the seal 14 away from the seal 16 generates a vacuum in the vacuum chamber 18 to cause eventual withdrawal of the holder 6 or 6b together with the needle into the syringe body 2 after use.

The forward end of the plunger 4 includes a radially-extending braking flange 20 which frictionally engages the inner surface of the body 2 in order to prevent non-intentional retraction of the plunger 4 under the influence of the vacuum created in the vacuum chamber 18. The braking flange 20 is a resilient flange defined at an outer edge of a conical wedge 22 formed at the forward end of the plunger. The conical wedge 22 is adapted to co-operate with the retaining pawls 8 for the needle holder in order to release the pawls 8 as will subsequently be described. The forward end of the plunger is also formed with an annular array of flexible pawls 24 arranged inwardly of the conical wedge 22. The pawls 24 are shaped to engage into an undercut groove 26 formed in the head of the needle holder in order to anchor the needle holder to the plunger 4 when the plunger 4 is in its forward position.

A removable stop ring 28 is mounted in an inner annular seat formed in the inner surface of the body 2 rearwardly of the fixed seal 16. The stop ring 28 is a split ring which is resiliently biased to an external diameter greater than that of the inner seat. An outer seat 30 for the stop ring 28 is formed in the body 2 rearwardly of the inner seat. The stop ring 28 has, on its internal surface, an annular groove 32 adapted to receive an annular rim 34 formed on the external surface of the plunger 4 towards the rear end of the plunger.

The syringe is supplied with the plunger 4 in its retracted position. In order to use the syringe, the plunger 4 is pushed inwardly to expel most of the air from the fluid-receiving chamber which is defined between the forward end of the plunger 4 and the needle holder 6 or 6b. Insertion of the plunger during this phase is limited by the stop ring 28, the rear edge of which engages a shoulder 36 at the outer end of the plunger 4. In this limit position, the annular groove 32 in the stop ring 28 is axially aligned with, and is engaged by, the projecting annular rim 34 on the plunger body whereby the stop ring 28 is releasably connected to the plunger 4. The stop ring 28 prevents insertion of the plunger 4 to its forwardmost position and hence prevents connection of the pawls 24 at the forward end of the plunger 4 with the groove 26 in the head of the needle holder. The plunger 4 can then be retracted to draw fluid into the fluid chamber of the syringe. It is to be noted that during this mode, the braking flange 20 on the plunger frictionally engages the inner wall of the body 2 in order to prevent retraction of the plunger under the influence of the vacuum generated within the vacuum chamber 18 during the insertion of the plunger. As mentioned above, at the end of the initial insertion stroke, the stop ring 28 is engaged by, and is connected to, the plunger. As the plunger is withdrawn to draw fluid into the chamber, the stop ring 28 is withdrawn with the plunger until the stop ring 28 is clear of the inner seat. When the stop ring moves into alignment with the outer seat 30, the inherent resilience of the stop ring 28 enables the stop ring to expand into the outer seat 30. The increased diameter of the outer seat 30 enables the stop ring 28 to expand to such a diameter that it disengages from the annular rim 34 on the plunger and is retained in the outer seat, as shown in the lower half of FIG. 1. A retaining lip 37 at the outer end of the outer seat 30 ensures that the ring 28 is retained within the seat in order to prevent accidental displacement of the ring 28 and possible jamming of the plunger.

When the required quantity of fluid has been drawn into the fluid chamber, the plunger is then depressed in order to expel air from the chamber in the usual manner and then to discharge the fluid into the patient. It is to be noted that as the plunger reaches the end of its injection stroke, the plunger is no longer subject to the influence of the stop ring 28 which is now in its larger diameter outer seat 30 and this enables the plunger to be moved into its fully forwards condition for discharge of substantially the entire contents of the fluid chamber. During the injection stroke, vacuum again builds up in the vacuum chamber 18, the effect of this vacuum being resisted by the braking flange 20 which frictionally engages the inner surface of the syringe body.

As the plunger nears the end of its injection stroke, that is beyond the stop position previously defined by the presence of the stop ring 28 when in its inner seat, the conical wedge 22 contacts the retaining pawls 8 in order to deflect these pawls outwardly beyond the retaining shoulder 10 on the needle holder and into engagement with the inner surface of the syringe body as shown in the lower half of FIG. 1: At the same time, the pawls 24 at the plunger move into snap-engagement in the undercut groove 26 in the head of the needle holder in order to connect the needle holder with the plunger. The rear ends 8a of the retaining pawls 8 constitute shear knives which, when the pawls 8 are deflected outwardly by the wedge 22, lie against the inner surface of the syringe body in order to contact the braking flange 20 and to deflect the flange 20 inwardly and rearwardly by plastic deformation of the flange, thereby reducing or removing the frictional contact between the braking flange 20 and the syringe body. When manual pressure is removed from the rear end of the plunger and with the braking action of the braking flange 20 removed or reduced consequent on its plastic deformation, the vacuum generated in the vacuum chamber 18 during the injection stroke acts to withdraw the plunger and thus the needle holder and needle which is now attached to the plunger. In the withdrawn position of the plunger, the needle is enclosed fully within the plunger body with no portion of the needle exposed for accidental contact. The needle holder is a relatively loose fit on the pawls 24 so that the axis of the needle holder and needle can incline relative to the syringe body whereby the tip of the needle will lie to one side of the syringe body and will be prevented by the sleeve 13 from accidental extension from the body. The sleeve 13 may also comprise a central iris structure held open by the needle holder when in its operative position. As soon as the needle holder is withdrawn by the plunger, the iris structure contracts or closes in order to close the central aperture of the sleeve 13 and thereby to prevent any access to the interior of the syringe body.

As no part of the needle is exposed after use of the syringe, the syringe can be disposed of in a conventional plastic bag. The absence of exposure of the needle also assists in preventing the spread of infection by contaminated needles.

The syringe shown in FIGS. 2a to 2e comprises a body 100 and a plunger 101. A needle holder 102 is mounted at the forward or inner end of the body 100. The needle holder 102 has at its forward end a cylindrical boss 103 inclined slightly to the longitudinal axis of the syringe body 100. A needle 104 is disposed on the boss 103 and is held in place thereon by a conventional U-lock fitting 105. Due to the inclination of the boss 103 the needle 104 is also inclined to the longitudinal axis of the body 100. The needle holder 102 has a bore 106 extending longitudinally through it and communicating at one end with an undercut recess 107, adapted to engage with a suitably shaped protuberance on the plunger as will be hereinafter described, and at the other end with the needle 104. A flange 108 on the needle holder 102 surrounding the undercut recess 107 engages behind an annular rib 109 on the inside wall of the body 100. A plurality of triangular sprags 111 project inwardly from the forward end of the body 100 and engage about the circumference of the needle holder 102. The engagement of the flange 108 of the needle holder 102 with the annular rib 109 of the body 100 and the engagement of the sprags 111 about the circumference of the needle holder 102 serve to securely locate the needle holder at the forward end of the body 100 until it is released therefrom by engagement with the plunger as will be hereinafter described.

The body 100 defines a substantially cylindrical bore 110 extending from the annular rib 109 which retains the needle holder 102 in place at the forward end of the body 100 to a second annular rib 113. Rearwardly of the annular rib 113 the body 100 increases in internal diameter through a frusto-conical zone 114 to a substantially cylindrical zone 115. The cylindrical zone 115 is directly connected to a second cylindrical zone 116 of slightly increased internal diameter which in turn is connected to a tapering zone 117 which tapers outwardly in diameter to the free end 119 of the body 100. Between the zones 116 and 117 the body is formed integrally with an annular collar 118. This collar 118 is molded extending rearwardly of the junction between the zones 116 and 117 and is then turned over to lie within zone 116, forming an inwardly directed annular abutment. The free end 119 of the body 100 is molded integrally with a pair of diametrically opposed stop members 121 joined by a thin flexible ring 122. The stop members 121 and ring 122 are also molded integrally with, and extend rearwardly of, the body 100 and are then turned over to lie within the zone 117.

A resilient annular braking and sealing member 123 is positioned within the zones 115 and 116 of the body 100. The member 123 includes a pair of inwardly directed annular sealing lips 124 extending radially inwardly from the member 123 and adapted to sealingly and slidably engage about the plunger 101. Rearwardly of the lips are three braking ribs 125, which could in another embodiment of the invention be replaced by rows of bosses which may serve the same purpose. The braking ribs are adapted to apply a braking force to the plunger 101. The radially outer surface of the member 123 carries at its forward end a circumferential rib 126. In the initial configuration of the syringe the member 123 is positioned with the rib 126 abutting against the forward end of the collar 118. The collar 118 then surrounds part of the member 123 and serves to compress the braking ribs 125 against the plunger 101.

The rearward end of the syringe body 100 is formed with a pair of outwardly extending finger grips 112 disposed in diametric opposition about the body 100.

The plunger 101 includes an elongate shaft 127 and at its forward end a radially extending sealing flange 128 in sealing engagement with the bore 110 of the body 100. At its forward free end the plunger 101 is formed with a protuberance 129 adapted to engage with the recess 107 in the needle holder 102. The protuberance 129 and recess 107 are so dimensioned that on engagement of the protuberance 129 in the recess 107 an inwardly directed flange 131 will be pivoted inwardly and forwardly by contact with the protuberance 129 which will cause the flange 108 on the needle holder to be pivoted rearwardly and inwardly to free the flange 108 from the annular rib 109 on the bore of the body 100.

The rearward end of the plunger 101 is formed with an enlarged head 132 which head 132 includes at its forward end a radially outwardly extending flange 133. The enlarged head 132 on the plunger 101 is preferably formed by heat reforming the rearward end of the plunger after the sealing and braking member 123 has been positioned on the stem 127 of the plunger 101.

Figures 2A, 2B, 2C:
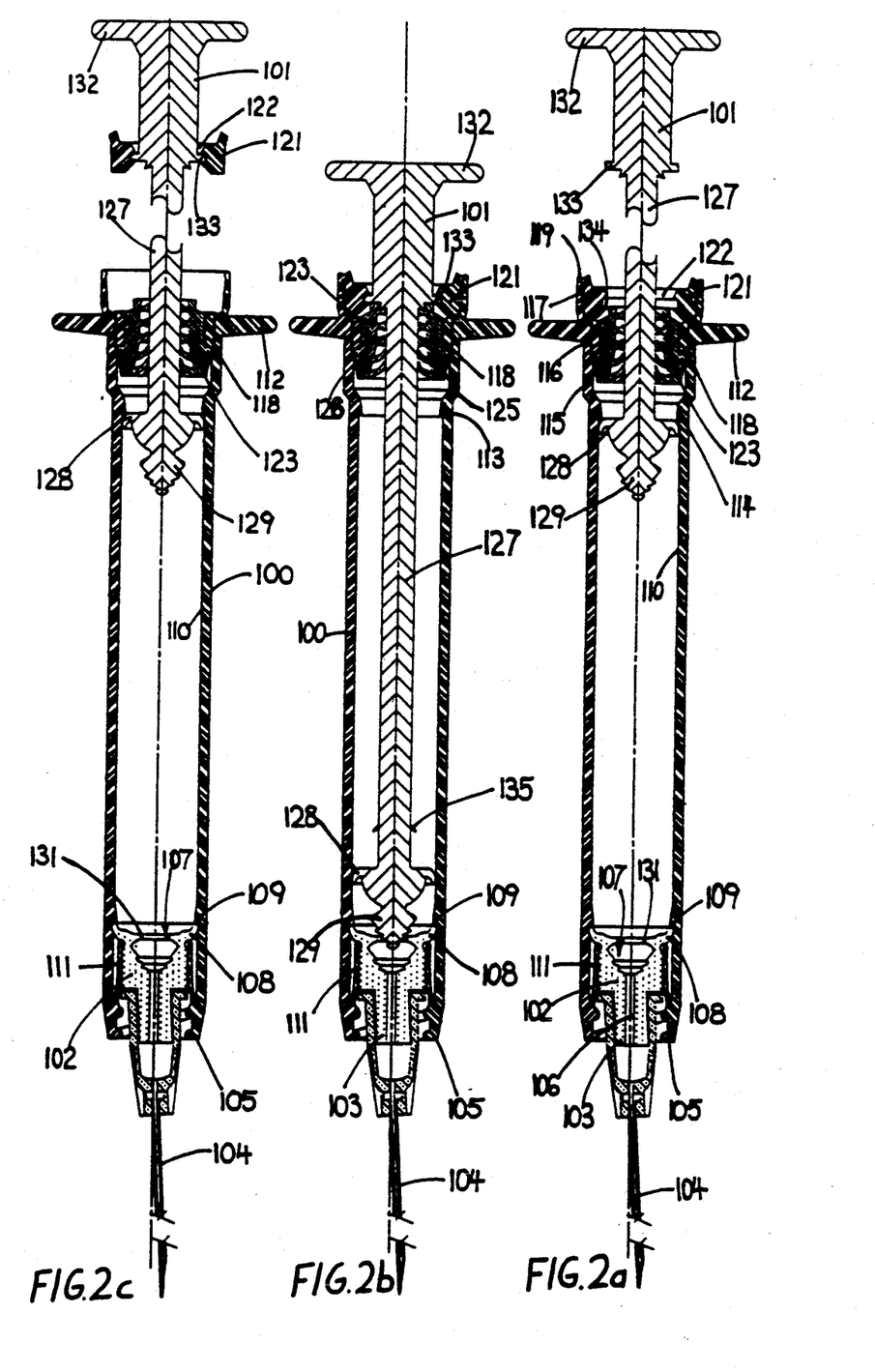

In use the syringe is shipped in the condition depicted in FIG. 2a. The plunger 101 is in its fully retracted position and the braking and sealing member 123 is surrounded by the collar 118 such that the braking ribs 125 are urged firmly against the shaft 127 of the plunger 101.

In order to draw an injectable fluid into the syringe the plunger 101 is depressed to the position shown in FIG. 2b. The plunger 101 is depressed until it is stopped by the engagement of the flange 133 on the head 132 of the plunger 101 with a pair of inwardly directed recesses 134 in opposed faces of the stop members 121. This engagement occurs when the protuberance 129 on the forward end of the plunger 101 is closely adjacent but not engaged with the undercut recess 107 in the needle holder 102. Subsequent retraction of the plunger 101 will draw an injectable liquid, into which the needle has been inserted, into the body 100 of the syringe. Such retraction will also shear the thin connection between the stop members 121 and the body 100 of the syringe. The dose of liquid in the syringe may then be adjusted, and air removed from the syringe, by depression of the plunger 101. The braking force applied to the shaft 127 of the plunger 101 is at this point sufficient to resist movement of the plunger 101 relative to the body 100 under the influence of the vacuum created between the braking and sealing member 123 and the sealing flange 128 as the plunger 101 is depressed into the body 100. Thus movement of the plunger 101 relative to the body 100 will only occur by manual application of force to the plunger 101 by the person using the syringe.

Figure 2D:
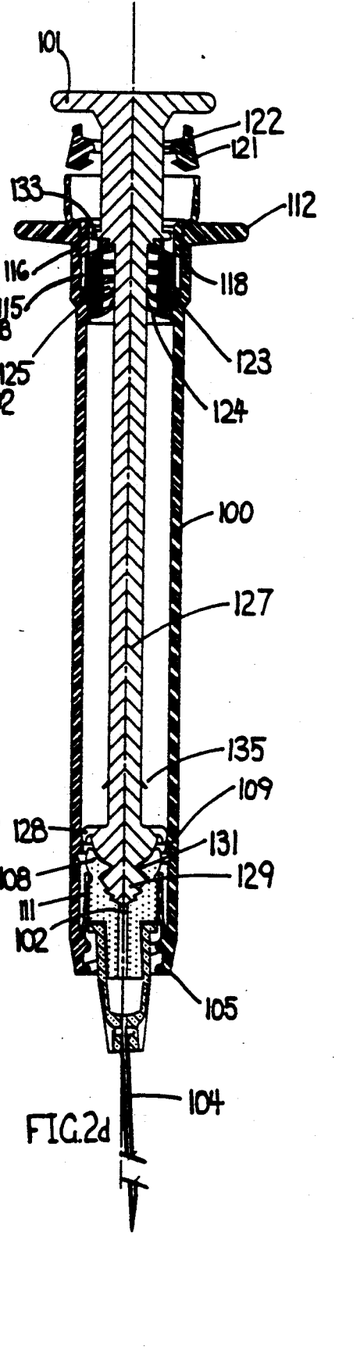

When an injection is to be given the needle is inserted into the patient in a conventional manner. This insertion is facilitated by the inclination of the needle 104 relative to the body 100 of the syringe as the body 100 is disposed at a more convenient angle to the skin of the patient, at least in the case of intravenous injections, than would be the case if the needle 104 was in axial alignment with the body 100 of the syringe. The plunger 101 is then depressed to inject the liquid into the patient. At the end of the plunger stroke the protuberance 129 will engage with the undercut recess 107 of the needle holder 102, as the earlier removal of the stop members 121 now allows the plunger 101 to be fully depressed. The engagement of the protuberance 129 with the undercut recess 107 causes the flange 108 on the needle holder 102 to be drawn radially inwardly free of the annular rib 109 in the body 100. As the protuberance 129 is entering the undercut recess 107 so the flange 133 on the head of the plunger 101 engages the rearward end of the braking and sealing member 123 pushing it into zone 115 of the syringe body 100 free of collar 118. The braking and sealing member 123 can expand radially within the zone 115 so that the braking pressure on the shaft 127 of the plunger 101 is reduced. When the syringe is withdrawn from the patient the vacuum created between the braking and sealing member 123 and the flange 108 will be sufficient to slowly draw the plunger 101 back into the body 100 of the syringe. The plunger 101 will also draw the needle holder 102, now freed from engagement with the body 100, and the needle 104 into the body. As the needle holder 102 is drawn into the body the free ends of the triangular sprags 111 will spring radially inwardly to form an iris precluding egress of the needle 104 outwardly from the now open forward end of the syringe body 100.

Figure 2E:
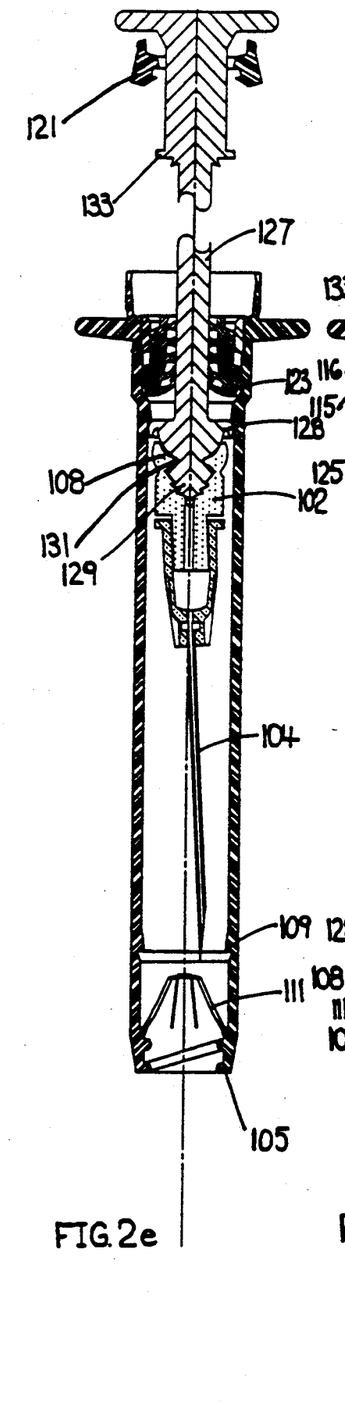

The vacuum pressure created in the syringe body 100 will be sufficient to draw the needle 104 fully into the body 100 behind the iris formed by the triangular sprags 111, and to engage radially outwardly directed fingers 135 on the shaft 127 of the plunger 101 behind at least the forwardmost one of sealing lips 124. Any subsequent use of the syringe is prevented firstly by the fact that the needle 104 is trapped within the body 101 by the sprags 111 and the inclination of the needle 104 and secondly by the fact that any depression of the plunger 101 will cause fingers 135 to drag the braking and sealing member 123 into the frusto-conical zone 114 of the body where the braking ribs 125 of the braking and sealing member 123 will be caused to tightly bind against the shaft 127 of the plunger 101.

Figure 3:
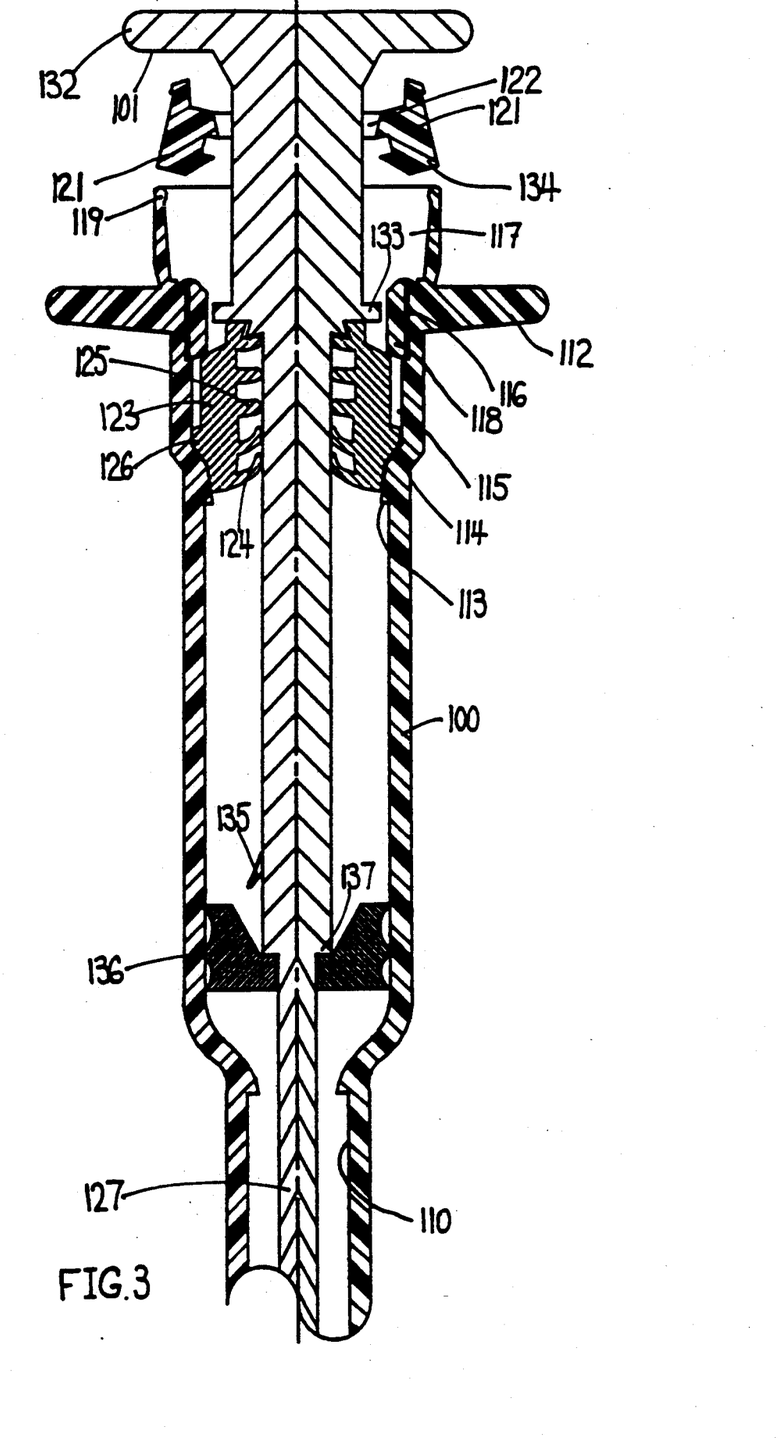
FIG. 3 is a longitudinal cross-sectional view through one end of a narrow base syringe according to another embodiment of this invention.

The arrangement of FIG. 3 shows the application of the present invention to a narrow bore syringe which would typically be used for giving an injection of about 1 ml of liquid to a patient. In this case the construction and operation of the syringe is as has been described with reference to FIGS. 2a to 2e except that the vacuum pressure is created between the braking and sealing member 123 and an additional sealing flange 136 mounted on the shaft 127 of the plunger 101 intermediate its ends. A step 137 on the shaft 127 causes the sealing flange 136 to move downwardly of the bore 110 as the plunger is depressed creating a vacuum between the sealing lips 124 and the flange 136. This vacuum will draw the flange 136 rearwardly when the injection has been completed and the flange 136 will carry the plunger 101 and the needle 104 rearwardly with it.

Figure 4:
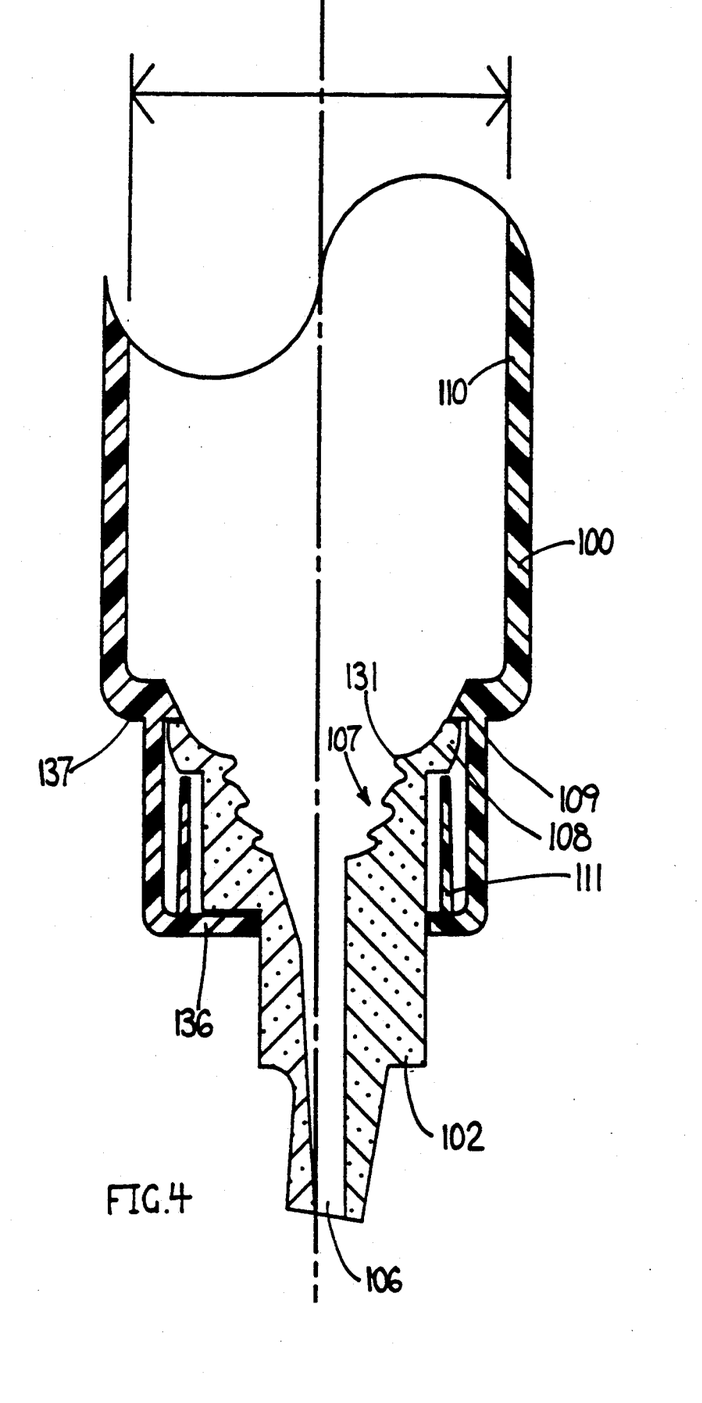
FIG. 4 is a longitudinal cross-sectional view through a needle holder and adjacent end of the body of a wide base syringe according to another embodiment of the present invention.

The arrangement of FIG. 4 shows the needle holder 102 positioned in a wide bore syringe. In this case the arrangement is as described with reference to FIGS. 2a to 2e except that the sprags 111 do not need to be molded so as to spring inwardly to form an iris upon withdrawal of the needle holder into the body 100 as the inturned flanges 137 and 138 are sufficient to prevent the needle 104 from being re-extended from the syringe once it has been drawn into the body 100.

The embodiments of the invention are given for the purpose of example only and are not intended to limit the broad scope of the present invention as defined by the claims. The needle holder 102 could if desired be held in place in the body 100 of the syringe by a friction fit without the need for the rib 109. Similarly the braking ribs 125 could be replaced by other configuration of means adapted to apply a braking effect between the plunger 101 and the syringe body 100.

I claim:
1. A syringe comprising:
   a body having a forward end, a rearward end, and a bore extending from the forward end to the rearward end;
   a needle holder slidably disposed within said bore proximate said forward end;
   a plunger having an end mounted slidably within said bore of said body, said plunger extending out of said rearward end of said body;
   connecting means for connecting said plunger to said needle holder on completion of an injection stroke of said plunger by injection pressure on said plunger so that subsequent retraction of said plunger withdraws said needle holder and any needle mounted thereon into a shielded position within said bore of said body;
   a first sealing member on said plunger extending radially into sliding sealing engagement with said body;
   a second sealing member on said body between said first sealing member and said rearward end of said body and extending radially with sliding sealing engagement into said plunger; and
   a chamber defined between said first and second sealing members, so that a vacuum is created within said chamber by movement of said plunger during the injection stroke and resultant movement of said first and second sealing members relatively apart, and said vacuum withdraws said plunger and said needle holder toward said rearward end after injection pressure on said plunger is removed.

2. A syringe as claimed in claim 1 and further comprising:
a plurality of pivotable fingers within said bore proximate said forward end of said body, said fingers being resiliently urged radially inwardly for forming an iris substantially occluding said forward end of said body when said needle holder is drawn into said bore.

3. A syringe as claimed in claim 1 wherein said bore has a longitudinal axis and further comprising:
means on said needle holder inclined relative to said longitudinal axis for inclining a needle thereon at an angle to said longitudinal axis.

4. A syringe as claimed in claim 1 wherein said connecting means comprises:
a protuberance at said end of said plunger within said bore; and
a complementary undercut recess in said needle holder engageable with said protuberance.

5. A syringe as claimed in claim 4 and further comprising:
a radially extending retaining flange on said needle holder;
complementary needle holder engagement means within said bore releasably engaging said retaining flange, and co-acting means on said plunger and needle holder for releasing said retaining flange from said complementary engagement means upon connection of said protuberance with said undercut recess.

6. A syringe as claimed in claim 1 and further comprising;
stop means on said body adjacent said rearward end of said body for arresting movement of said plunger during a preparatory forward stroke of said plunger for preventing said connecting means from connecting said plunger to said needle holder on completion of said preparatory stroke; and
stop engagement means on said plunger adapted to engage said stop means on said preparatory forward stroke and render said stop means inoperative by a subsequent rearward stroke of said plunger so that said stop means does not impede said plunger during the injection stroke.

7. A syringe as claimed in claim 6 wherein;
said bore forms an inner seat on said body;
said stop means comprises an abutment removably disposed on said inner seat; and
said stop engagement means engages said abutment during the preparatory forward stroke so that said abutment is sheared from said body by a rearward stroke of said plunger.

8. A syringe as claimed in claim 7 wherein said connecting means comprises:
a protuberance at said end of said plunger within said bore; and
a complementary undercut recess in said needle holder engageable with said protuberance.

9. A syringe as claimed in claim 8 and further comprising:
a radially extending retaining flange on said needle holder;
complementary needle holder engagement means within said bore releasably engaging said retaining flange, and co-acting means on said plunger and needle holder for releasing said retaining flange from said complementary engagement means upon connection of said protuberance with said undercut recess.

10. A syringe as claimed in claim 9 and further comprising:
a plurality of pivotable fingers within said bore proximate said forward end of said body, said fingers being resiliently urged radially inwardly for forming an iris substantially occluding said forward end of said body when said needle holder is drawn into said bore.

11. A syringe as claimed in claim 10 wherein said bore has a longitudinal axis and further comprising:
means on said needle holder inclined relative to said longitudinal axis for inclining a needle thereon at an angle to said longitudinal axis.

12. A syringe as claimed in claim 6 wherein said connecting means comprises:
a protuberance at said end of said plunger within said bore; and
a complementary undercut recess in said needle holder engageable with said protuberance.

13. A syringe as claimed in claim 1 and further comprising:
resilient braking means for retarding retraction of said plunger disposed within a space between said bore and said plunger, said braking means being disposed on one of said body and plunger and in slidable engagement with the other of said body and plunger for providing a braking force sufficient to retard but not stop retraction of said plunger.

14. A syringe as claimed in claim 13 wherein:
said braking means further comprises braking modifying means on said body and cooperating means on said braking means; said braking modifying means being adapted to bear against said cooperating means so that relative movement therebetween during the injection stroke reduces said braking force after the injection stroke.

15. A syringe as claimed in claim 14 wherein:
said bore comprises zones having different internal diameters;
abutment means are provided on said plunger engageable with said braking means during the injection stroke; and
said resilient braking means comprises a resilient cylindrical member slidable on said body and having rib means resiliently bearing against said plunger for exerting a braking force, said resilient cylindrical member being longitudinally moveable within said zones of different internal diameter by said abutment means for reducing the braking force on said plunger.

16. A syringe as claimed in claim 13 wherein said connecting means comprises:
a protuberance at said end of said plunger within said bore; and
a complementary undercut recess in said needle holder engageable with said protuberance.

17. A syringe as claimed in claim 13 wherein said bore has a longitudinal axis and further comprising:
means on said needle holder inclined relative to said longitudinal axis for inclining a needle thereon at an angle to said longitudinal axis.

* * * * *